United States Patent
Gavriely et al.

(10) Patent No.: US 7,819,814 B2
(45) Date of Patent: Oct. 26, 2010

(54) ACOUSTIC ASSESSMENT OF THE HEART

(76) Inventors: Noam Gavriely, 11 A Sinai Avenue, Haifa (IL) 34331; Nathan Intrator, 12 Kfar Yona St., Tel Aviv (IL) 60953

( * ) Notice: Subject to any disclaimer, the term of this patent is extended or adjusted under 35 U.S.C. 154(b) by 530 days.

(21) Appl. No.: 10/532,178

(22) PCT Filed: Oct. 21, 2003

(86) PCT No.: PCT/IL03/00858

§ 371 (c)(1),
(2), (4) Date: Apr. 21, 2005

(87) PCT Pub. No.: WO2004/035137

PCT Pub. Date: Apr. 29, 2004

(65) Prior Publication Data

US 2006/0047213 A1 Mar. 2, 2006

(51) Int. Cl.
*A61B 5/02* (2006.01)
*A61B 5/08* (2006.01)
*A61B 5/04* (2006.01)
*A61B 7/00* (2006.01)
*A61N 1/00* (2006.01)

(52) U.S. Cl. ............... 600/528; 600/484; 600/513; 600/586; 607/18

(58) Field of Classification Search ......... 600/481–507, 600/509, 513, 514, 528, 586; 607/17, 20, 607/25
See application file for complete search history.

(56) References Cited

U.S. PATENT DOCUMENTS

| 5,957,866 A * | 9/1999 | Shapiro et al. ............... 600/586 |
| 6,629,937 B2 * | 10/2003 | Watrous ..................... 600/586 |
| 2003/0220578 A1 * | 11/2003 | Ho et al. ..................... 600/521 |

* cited by examiner

*Primary Examiner*—Charles A Marmor, II
*Assistant Examiner*—Christian Jang

(57) ABSTRACT

A non-invasive method and apparatus for monitoring of the function of the heart and lungs in vulnerable patients. An analysis of the activity of the heart is made in correspondence to the respiratory system. Using the method of the invention, precise tracking of the changes of the mutual heart-lung interactions cycle are made, enabling better definitions of heart conditions. Within breath variability factor is introduced for tracking heart condition. Failing heart assisting methods and improved diagnostic methods are facilitated using the monitoring system of the invention.

3 Claims, 3 Drawing Sheets

ACOUSTIC ASSESSMENT OF THE HEART

TECHNICAL FIELD OF THE INVENTION

The present invention relates to non-invasive cardiac and respiratory monitors. More specifically, diagnostic tools and methods for evaluating the heart and respiratory system and improving the function of the failing heart are disclosed.

BACKGROUND OF THE INVENTION

Cardiopulmonary monitoring of clinically unstable patients is essential for early detection of potentially life threatening changes in the functionality of the heart or respiration. Cardiopulmonary monitoring is presently done on hospitalized patients in critical care, such as intensive care units (ICU), coronary care units (CCU) and peri-operatively as well as in other specialized sections of the hospital. Certain types of cardiopulmonary monitoring are also performed on patients outside the hospital, such as patients who suffer from asthma, high blood pressure, or cardiac arrhythmias. Cardiopulmonary monitoring is also used during exercise performance tests of patients and athletes. Clearly, monitoring and early detection of impending catastrophes are highly desirable in clinical medicine.

Continuous monitoring of cardiopulmonary wellbeing is presently focused on physiological parameters that characterize, individually, the activity of the heart and respiration. These parameters include monitoring of the electrocardiogram, blood pressure in the arterial, venous and pulmonary circulations and cardiac output for assessing the cardiovascular system. The airway pressure, respiratory rate, tidal volume, flow rate, pulse oximetry, exhaled $CO_2$, and esophageal pressures are the respiratory parameters that are commonly monitored. More recently continuous overnight monitoring of breath sounds was introduced to detect and quantify wheezing activity in asthmatics. Additional methods were introduced to monitor patients inflicted with congestive heart failure (CHF) to identify early decompensation. These methods are based on continuous monitoring of the electrical impedance of the thorax, but have not generated reliable levels of sensitivity and specificity. Monitoring of respiratory crackles has also been used as an early sign of lung congestion.

The activities of the heart and the lungs are well known to be closely interrelated. The heart rate, blood pressure and blood flow into and out of the heart are influenced by the breathing cycle. The pressure inside the chest becomes more negative during inspiration to enable inflow of air into the lung alveoli. This sub-atmospheric pressure also affects the heart, blood vessels and blood flow. In particular, the increased intrathoracic negative pressure expands the right atrium and ventricle, dilates and elongates the blood vessels, amplifies the ventricular filling and changes the position of the inter ventricular septum. In addition, the changes in lung volume modify the afferent neuronal activity in the vagus nerve, leading to modulation of the heart rate during respiration. During quiet breathing the intrapleural pressure decreases from about −3 mm Hg to about −6 mm Hg. This causes dilation of the intrathoracic segment of the vena cava, increased venous return to the right atrium and ventricle. The increased diastolic filling of the right ventricle amplifies its stroke volume into the pulmonary circulation by the well-known Starling mechanism. At the same time, the inspiratory displacement of the abdominal content by the contracting diaphragm increases the intra abdominal pressure, which further pushes blood into the thoracic cavity. The intrathoracic pressure changes during breathing also influence the output of the left ventricle, but to a lesser degree. During deep breathing, or in pulmonary diseases that affect the mechanical properties of the airways and the lung parenchyma these, respiratory swings of flow, resistance and volume are greatly exaggerated (Mountcastle V. O. Medical Physiology, $12^{th}$ ed. Mosby Company, St. Louis 1968).

Positive pressure ventilation squeezes the pulmonary capillaries and increases the resistance to blood flow through the lungs. These pressures may diminish the output of the right ventricle due to increased afterload, while at the same time reducing the output of the left ventricle due to fall in its diastolic filling and preload. These phenomena are known to result in wide fluctuations of the cardiac output and blood pressure. Similar fluctuations are also seen during resisted breathing, cough and isometric muscle straining.

Monitoring of heart sounds is well known to medicine and physiology for many years, even before the invention of the stethoscope by Laennec in 1819. The first and second heart sounds are associated with closing of the atrioventricular and ventricular outlet valves, respectively. They are loud and distinct sounds with somewhat different amplitude and template in different areas of precordial auscultation. The first and second heart sounds are modified, and sometimes are even completely missing during diseases of the heart or the lungs. Additionally, the $3^{rd}$ and $4^{th}$ heart sounds are well known to be associated with defects of the left ventricular filling during diastole. Rumbling sounds heard in between the first and second sounds (systole) or the second and first sounds (diastole) are appropriately called systolic and diastolic murmurs, respectively and are associated with abnormal blood flow through the narrowed or malfunctioning heart valves. Information on heart sounds, phonocardiography and the art of interpretation of heart sounds is readily available in many text books and articles, such as in "Rapid interpretation of heart sounds and murmurs" by Emanuel Stein, Abner J. Delman (Editors), Williams & Wilkins, 1997, 4th edition, the contents of which are incorporated herein by reference.

The respiratory changes of cardiac activity are well known. In particular, the phenomenon of "Pulsus Paradoxus" is a recognized sign of severe asthma and airway narrowing. It is defined as a decline of greater than 12 mm Hg (in some texts 20 mm Hg) in the systolic blood pressure during inspiration. Detection of Pulsus Paradoxus in a dyspneic patient is an ominous sign that calls for aggressive and immediate intervention. On the other hand, cardiac arrhythmia, the acceleration and deceleration of the heart rate during the respiratory cycle is often a benign and normal phenomenon, particularly in young children. The only available information on the effect of respiration on the heart sounds per-se is on the width of splitting of the second heart sound and on certain cardiac murmurs. Otherwise, no information is available on the changes in the heart sounds induced by respiration and on the extent of these changes during various cardiopulmonary conditions.

The failing heart condition is a cause for severe morbidity and mortality rates. This condition can be helped by a broad range of assist methods. These include pharmaceutical agents (e.g., digitalis and other positive inotropic agents), mechanical support (e.g., intra aortic counter pulsation, and intravascular coronary artery stent), and various types of electrical stimulation (e.g., ventricular resynchronization therapy, Guidant's Contak CD, Medtronic's multi electrode epicardial pacing, Impulse Dynamics' timed refractory period current). All heartbeat synchronized methods must be monitored as regards their performance. This feedback can determine if, and to what extent the assistance is effective. Such monitoring is either performed in intervals (e.g., by periodic determination of the left ventricular ejection function), or continuous (e.g., by monitoring the left ventricular pressure—Remon Medical Technologies LTD of 7 Halamish Street, Caesaria Industrial Park, 38900, Israel). To be effective, the mechanical and electrical assist methods should be synchronized with the cardiac cycle so that they can be activated at specific phases of the cardiac cycle. For example, in U.S. Pat. No. 6,285,906 the contents of which are incorporated herein by reference, impulse dynamics provides current stimuli at certain precise phases of the heart cycle. To do so, most methods use the EKG (electrocardiographic) signal to find the appropriate timing within the cardiac cycle for activation of the assistance. However, the EKG may not provide sufficiently detailed or accurate information about the timing cardiac cycle, or may be contaminated by electromagnetic noise.

DETAILED DESCRIPTION OF THE INVENTION

Figure 1:
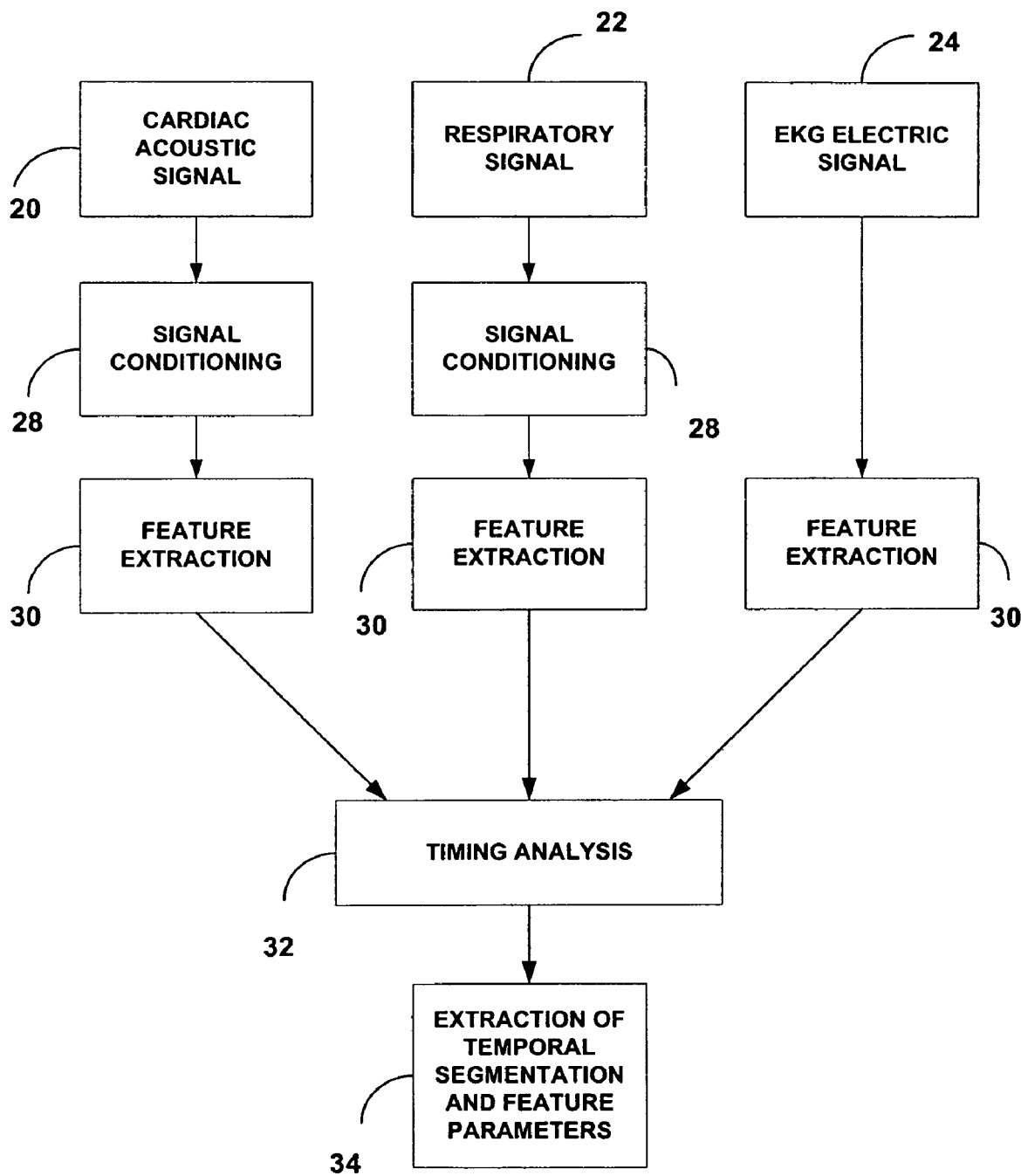
FIG. 1. is a schematic description of the signal collection and processing device providing synchronized features of the cardiac activity.

The present invention provides a novel method for monitoring the interrelated functionality of the heart and the respiratory system by tracking the changes in cardiac sounds with respect to the activity of the heart during the respiratory cycle. A novelty of the new approach is that the timing of each heart contraction within the breathing cycle is used as a cardinal parameter in the analysis of the heart sounds relative to the electrocardiographic signal. By doing so, the heart sounds generated during similar segments of the respiratory cycle, for example, the first part of inspiration, are analysed together to generate respiratory synchronized stable templates and features of the heart sounds and their interaction with the EKG. Thus, the extent of changes in EKG—modulated heart sounds parameters during each phase of the respiratory cycle may be tracked over time to detect variability of the breathing related swings that indicate worsening of the status of the cardiopulmonary system. In addition, the invention facilitates tracking of the stable synchronized cardiac sounds features over time that are indicative by themselves of the well-being of the mechanics of the heart and lungs. It is further disclosed that the determination of the stable synchronized cardiac sounds features is classified by the timing and template of the EKG. Together, these new methods provide valuable information on the status and mechanics of the complete cardiopulmonary system.

The invention overcomes two major hindrances to extraction of stable features from heart sounds: the variability of the cardiac sounds during the respiratory cycle and changes in the sounds caused by variability of the electrical activity of the heart. The new method extracts features such as amplitude, duration, frequency content, template and chirp components of the heart sounds and clusters these features with respect to their timing in the respiratory cycle and/or their underlying EKG morphology. This method preserves the attributes of the cardiac acoustic signal that are otherwise eliminated or greatly diminished by grouping the sounds or their features without respect to their respiratory timing and EKG, as is currently learned by the existing art. The extraction of synchronized stable features greatly diminishes their stochastic variability, so that any changes in the deterministic components of the heart sounds, such as those caused by changes in the mechanical activity of the heart, are more readily and accurately detected and characterized. The acoustic properties of the heart sounds reflect the mechanics of the cardiac contraction, the integrity of the cardiac structure and dynamics of flows, volumes and pressures in the cardiovascular system. Therefore, detection of changes in the synchronised stable sounds relative to a baseline may be used to alert the patient, his or her caregivers, or an automated algorithm or device that can be prompted to provide a remedy to the patient's condition. This new method, while preserving complete non-invasiveness, provides far more comprehensive monitoring of the patient than the current existing methods such as the EKG.

The grouping of synchronised stable features of the heart sounds with or without respect to the EKG template defines a baseline extent of Within Breath Variability (WBV). Any changes of the extent of variability of the sounds or their features within the respiratory cycle relative to a previous period, such as the baseline, can be readily and accurately detected. These alterations of the WBV may be caused by increased pressure swings within the chest due to altered breathing pattern or changes in the resistance, compliance or other mechanical properties of the lung. Such changes are often seen in asthma patients, patients inflicted by congestive heart failure (CHF), patients who are artificially ventilated, anaesthetised, or otherwise critically ill.

Analysis of the Heart Sounds

In FIG. 1 to which reference is now made the main stages in collecting and processing of the signals, in a preferred embodiment of the invention are shown. Cardiac acoustic signals 20, respiratory acoustic signal 22 and EKG electric signal 24 are collected by the appropriate detectors. The cardiac acoustic signal and the respiratory acoustic signal are separated and conditioned, by module 28, which includes in a preferred embodiment of the invention filtering, denoising, amplification, multi-sensor analysis for removal of background noise and recording artifacts. Feature extraction module 30 of the invention performs segmentation. Heart sounds are segmented into S1, S2, S3, S4, the breathing activity is segmented into the Heart sounds are segmented into S1, S2, S3, S4, the breathing activity is segmented into five respiratory stages; first half of inspiration, second half of inspiration, first half of active expiration, second half of active expiration and the post expiratory pause if present, and the EKG signal is segmented into its components; P, QRS, T waves. The segmented input data undergo timing analysis by module 32. Temporal segmentation feature parameters are extracted from the segmented data by module 34. The parameters are estimated individually from heart sounds appearing at the different respiratory stages. The EKG signal is also analyzed with respect to the respiratory stages.

Heart sounds are acquired via a single microphone or a plurality of microphones located on the chest, back and/or neck of the patient. After signal conditioning that includes pre-amplification, the signal is band-pass filtered so that the respiratory component may be separated from the heart sounds. The isolated sound structures are then detected in the heart sounds signal and classified as S1, the first heart sound, and S2 the second heart sound. The degree of isolation (which is related to the beating rate) is estimated earlier from the data using a density plot of the inter-beat duration. A temporal window, related to the time interval variability, is used to distinguish between S2 and S1. Further validation of the S1/S2 segmentation may be provided by the EKG signal where the timing of S1 is known to correlate with the QRS sequence and the timing of S2 corresponds to the T wave. After the different sounds are segmented, an attribute corresponding to the respective respiratory cycle is attached to each of them, so that they can be further collected into groups with their corresponding timing within the respiratory cycle. Averaging the different sounds and/or their attributes in the corresponding respiratory cycle forms adaptive templates. Averaging is performed within each timing interval on the raw signal, the frequency content representation, and on a time-frequency representation obtained by short time Fourier transform, Wigner distribution analysis or a more adapted time-frequency representation using continuous wavelet transform or best basis and discrete wavelet representation. The latter methods include internal denoising (compression) which is achieved by removing the low energy coefficients from the transformed signal representation before performing the inverse transform.

The time-frequency representation can be used for parameter estimation of the chirp properties (mainly S2). These properties include the chirp slope, namely the frequency modulation of the signal, start and stop frequency as well as slope, and the amplitude changes in the signal. Properties related to the time-frequency representation are extracted using conventional curve fitting techniques. Features related to the amplitude changes, e.g. increase in negative amplitude of S2, frequency content as is recorded by Fourier transform, and instantaneous frequency changes which is recorded in the time-frequency representation. The parameters corresponding to each of the above categories, and their variability may be empirically estimated from the data and compared to a data base or baseline values of these parameters. The variability together with the estimation of the mean, may further be used for the estimation of statistically significant changes in each of the parameters, both during a respiratory cycle and when compared with a normal baseline of the specific patient or of previously recorded and labeled data.

The separation of the deterministic and stochastic signal components is done during entropy-based denoising, e.g. with wavelet or best basis representation. The wavelet coefficients with smallest variance, which correspond to smallest contribution to the energy of the collection of heart sounds, are set to zero. This parameter shrinkage removes the part of the signal that is independent of the heart sounds and can be considered noise.

A non exhaustive list of temporal segmentation parameters and features, with respect to the respiratory stages extracted from the heart sounds, respiratory cycle and EKG useful in the cardiac assessment of the invention is provided next:

1. Amplitude and energy of S1 and S2 in each segment, (peak and RMS) where S1 and S2 are the first and second heart sounds, respectively.
2. Timing of S1 and S2 relative to the EKG and relative to each other whereas the EKG represents the electrical activity of the heart, measured with skin-surface electrodes.
3. Delta time between occurrence of S2 and S1 and occurrence of S1 and the S2 of the previous heart cycle.
4. Delta time between the occurrence of S1 and occurrence of the QRS wave.
5. Delta time between the occurrence of S2 and occurrence of the P wave.
6. Delta time between the occurrence of the P wave and the R wave.
7. Frequency content and instantaneous frequency content of S1 and S2.
8. Cord length of S1 and S2.
9. Polarity of first and largest component of S1 and S2.
10. Amplitude incline and damping (decaying) rate constant of S1 and S2.
11. Chirp parameters of S1 and S2.
12. Duration of whole cardiac cycle (reciprocal of the heart rate) as well as of each heart sound segment (i.e. of S1, S2, S3, S4, or murmurs).
13. Signature (or shape) specific for each sensor by using signal processing methods and/or polynomial fit. Differentiate between deterministic elements (e.g. S1-4) and stochastic elements such as murmurs and/or artifacts. Determine separately for each frequency range. Obtain template pattern of the heart sounds signature for each segment of the respiratory cycle.
14. Cross correlation between various precordial sites. An expansion of this is creating a dynamic acoustic map of the anterior chest using many sensors, each displayed on an array with brightness indicating amplitude and color (s) indicating the frequency content. The dynamics of the changing map can be tracked for changes during the respiratory cycle.
15. Calculate the deconvolution of the heart sounds/ballistographic signal in order to estimate the mechanical activity at the source that generates the signs.
16. An AM/FM Modulation decomposition of the heart sound to analyse independently amplitude changes and frequency changes in the heart sounds.
17. Amplitude multiplied by the width of each heart sound which is an approximation to the temporal length of the heart sounds times the peak amplitude of each heart sound. Energy of some components of the heart sound as is measured in a time/frequency representation which can be adapted to the signals.

Using the above parameters and features, deterministic and stochastic components of the features and parameters are extracted. This defines the acceptable boundaries for each feature and parameter. Such boundaries are determined by the extent to which the parameters vary whilst the patient is in stable condition. In a preferred embodiment, these boundaries are defined by the mean and n×SD of each parameter and feature for each the respiratory stages, where n is 2 for example. In particular, the (potentially non-linear) boundaries of the hyper-parameter space of the full set of the parameters are determined. Thus, for example, it is possible that a patient can be at a point where each of the parameters and features is within the defined boundaries, but the full set of parameters is outside of the boundaries.

A probabilistic model, which is estimated in a preferred embodiment, via calculation of maximum likelihood, is applied to the processed data to further refine the model estimation. This binds together the temporal progress from one respiratory stage to another (via a hidden Markov model). At this stage, additional information from other sources such as blood pressure, oxygen saturation, patient weight, chest electrical impedance and other means, is fused. The full temporal model and set of segmented features are then analyzed to determine scoring of deviation from normality, or from the acceptable patients' boundaries.

The probabilistic analysis assumes a Gaussian distribution to the continuous features of the model and a binomial (sometimes multinomial) distribution to the categorical parameters. Following the estimation of the mean and standard deviation, significance or abnormality of an observed features may be determined and using a probability model which takes into account the probability of a collection of features (taken from an already collected and soon to be collected data), one can estimate the probability of various abnormal events.

Figure 2:
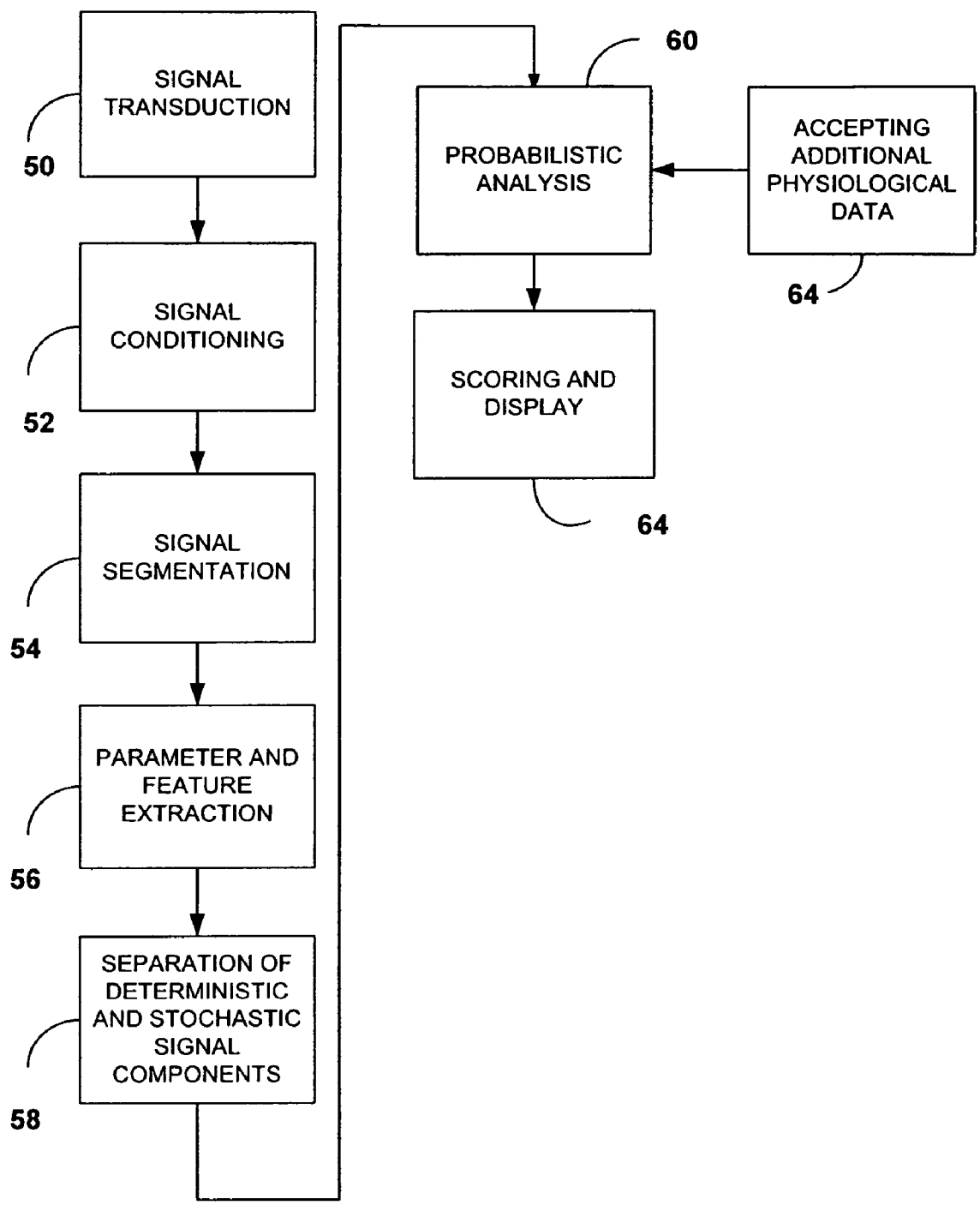
FIG. 2. is a schematic description of the entire process in accordance with a preferred embodiment of the invention, performing probabilistic analysis.

In FIG. 2 to which reference is now made, the whole sequence of steps from the signal transduction to model display is described schematically. In step 50 signals are transduced to produce a corresponding electric current. In step 52 the signals are conditioned. In step 54 the signals are segmented to express the segments of the physiological rhytmicity. In step 56 Parameters are extracted, and in step 58 the deterministic components are separated from the stochastic components. In step 60 the probabilistic analysis is performed, accepting physiological data at step 62, and in step 64 scoring and display are provided. Although not shown, the probabilistic analysis performed reflects on the signal segmentation to influence the segmentation process.

Sensors for Collecting Signals of the Heart and Respiratory System

In general, apart from the ubiquitous EKG which senses electrical signals of the body, all other sensors taking part in the signal collection in accordance with the present invention are acoustic or mechano-acoustic sensors. Such sensors transduce mechanical pressure, or acoustic energy to electrical energy further to be analyzed electronically. Acoustic sensors for sensing activity of the heart to determine cardiac mechanical performance, which include typically rhythmicity, fine cardiac temporal cycle variability and muscle contractility, can be patched on the patient's chest or can be implanted subcutaneously. Conditioning respiratory activity sounds and respiratory activity mainly for the determination of respiratory rhythm is preferably performed using impedance plethysmography. Several sensors can be used concomitantly for obtaining data about the sounds.

Electronic Hardware for Processing the Data and Providing Diagnostic Aids and Control Signals Transduced electric signals from the sensors, as well as EKG signals, are collected by data collecting hardware, sampled and digitized on a dedicated processor or in a computer. All processing and statistical calculations and model assessment are done in the computerized environment. A GUI or a printer is typically used to produce a report to the medical team in charge. In that case that control signals are required, this can be supplied by a controller linked to the processor or computer wherein the processing is performed. If more than one sensor is used for obtaining sounds data, a procedure for correlation between the sensors may be implemented. The implementation of such a procedure is typically carried out for reducing noise.

Medical Uses of the Invention

A simple example of the method of the invention includes segmenting the breathing cycle into exhaling and inhaling segments, and recording contracting heart sound at these inhaling and the exhaling segments. Sound amplitude samples are collected and then averaged, average A for the set of samples representing the exhaling segment period and average B for the set of samples representing the inhaling segment period. Statistical difference is calculated between the averages A and B, providing evidence regarding quantitative difference in magnitude between the two sets. The physiological significance of the difference is such that the larger difference is indicative of a pronounced tendency of the heart to be limited by the expanding lungs.

These parameters and changes may be used to detect early changes associated with pulmonary and/or hemodynamic alterations. These include CHF (changes in the heart's mechanical activity, the lungs specific gravity (density) and increased fluctuations of intrathoracic pressure); mechanical ventilation (changes in PEEP, airway resistance), changes in hydration and blood volume (shock) (cardiac mechanical activity, increased breathing activity), hypertension (increased cardiac mechanical activity), myocardial infarction (changes in cardiac contraction sequence).

The detection of each of the above-listed conditions is done by comparing the respiratory synchronized cardiac sounds or features thereof to a patient-specific baseline, or to a template consisting of data from an aggregate of normal and abnormal patients. A system of the invention or any system using the method of the invention are either therapeutic or diagnostic.

Cardiac Synchronization Methodology and Usage in Diagnostic and Therapeutic Devices Assessment of the mechanical condition of the heart performed in accordance with the invention can be used to help treating the failing heart. An acoustic heartbeat synchronized method comprises, in accordance with the present invention, one or more sensors of heart sounds that can pick up and transduce the heart sounds of a patient into electrical signal and means for amplifying the signal, typically but not necessarily a sensor for breathing activity and means for synchronizing the signals. The heart sounds timing signal can be used to trigger the activity of a heartbeat synchronized device, either directly or with a delay. Such delay may be pre-determined or modified automatically, based on information on the heart sounds amplitude, the interval between them, or their amplitude and frequency content.

Figure 3:
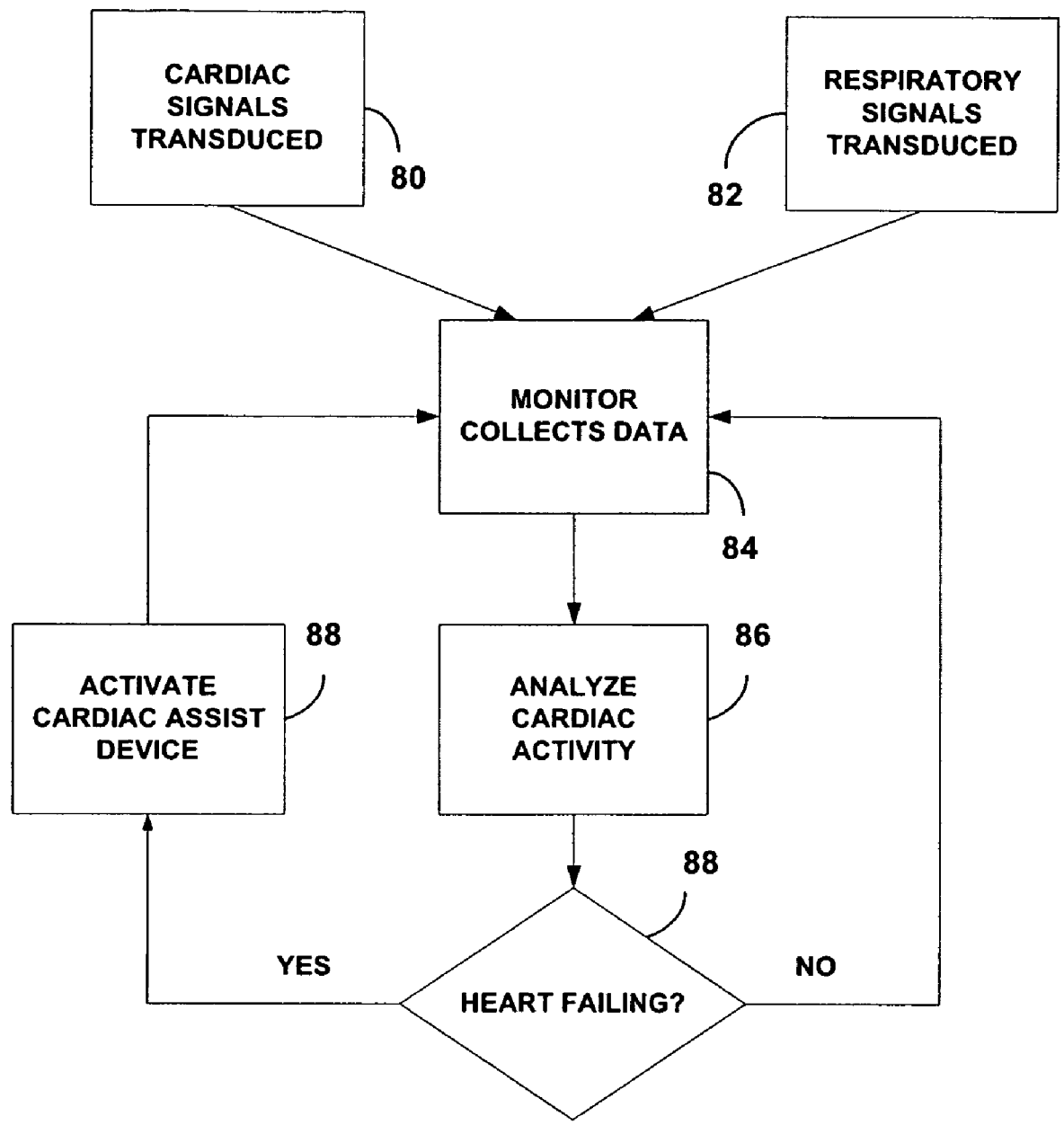
FIG. 3. is a schematic description of the decision loop involving heartbeat synchronized control in accordance with the invention.

In FIG. 3, to which reference is now made, an automated control mechanism a heartbeat synchronized device using a synchronization algorithm of the present invention, is shown. Acoustic cardiac signals are transduced 80 and respiratory signals 82 are transduced to be collected by the monitor 84. Subsequently, they are processed at step 86 by the method of the invention to extract accurate parameters of the heart. If the heart is regarded failing at diagnostic step 88, the heartbeat synchronized device is activated.

The heart sounds timing signal is used to actuate a demand-type or synchronized cardiac pacemaker. This pacemaker is chronically implanted, or temporarily used to defibrillate a fibrillating heart, such as used in automatic or manually triggered electric defibrillators. Several therapeutic and diagnostic systems can benefit from using the heartbeat synchronization concept embodied in the invention. Such systems are intra-aortic balloon pump, left ventricular cardiac assist device, coronary angiography diagnostic devices, cardiac imaging devices such as, but not limited to, CT, MRI and SPECT diagnostic technologies.

Monitoring Variability Changes

The grouping of synchronized stable features of the heart sounds with or without respect to the EKG template defines a baseline extent of within breath variability (WBV). Any changes of the extent of variability of the sounds or their features within the respiratory cycle relative to a previous period, such as the baseline, can be readily and accurately detected. These alterations of the WBV may be caused by increased pressure swings within the chest due to altered breathing pattern or changes in the resistance, compliance or other mechanical properties of the lung. Such changes are often seen in asthma patients, patients inflicted by congestive heart failure (CHF), patients who are artificially ventilated, anesthetized, or otherwise critically ill. When such changes are found they can be used to alert the patient, his or her caregivers, or an automated algorithm or device that can be prompted to provide a remedy to the patient's condition.

Short Duration Analysis

Known in the art are changes in the duration of each heartbeat in association with the breathing cycle. These changes are usually detected by measuring the distance between consecutive "R" waves in the EKG that are called "the R-R interval". The changes in the duration of the R-R interval over time are referred to as heart rRate variability" (HRV). HRV is considered as indicative of the activity of the sympathetic and parasympathetic control of the heart. It is substantially reduced in gravely ill patients. Recently, changes (reduction) in HRV have been associated with particulate matter (PM) air pollution and are believed to be an important mechanism in the increased mortality due to PM pollution. Other conditions, such as the sleep apnea syndrome, chronic cardiac ailments and the use of certain medications are also known to be associated with changes in HRV.

In accordance with the present invention, analysis of the short-term duration changes of systolic time (Tsys) and diastolic time (Tdias) is performed and studied with the respiratory cycle as well as the other amplitude and signal morphology features that have been discussed above. Of particular interest are correlation between short term changes which are indicative of a well-heart being such as increase in Tsys which leads to a an increase in the amplitude and sharpness of S2, indicating an increase in duration that is due to more blood flow into the heart, or a negative correlation between Tsys and Tdias, indicating is more elaborated breathing (possible airway obstruction) but healthy heart dynamics, vs. changes in Tsys that are not correlated with Tdias and vice versa.

The method of the invention can be used to differentiate between inhalation and exhalation phases of the respiratory cycle. It can also be used to determine the template and variations of S3, S4 and cardiac murmurs.

Use of the Invention in Irregular Breathing Instances

The method of the invention can be applied in the course of irregular breathing. Forced breathing interruptions are examples in which the method of the invention may be used to analyze the condition of the heart. More particular examples for such irregularities are breath hold after deep respiration and Valsalva maneuver while agonal respiration is a pathological instance of interrupted respiration.

Use of the Method of the Invention in Diagnosing Extra Cardiac Blood Vessels

The method of the invention can be applied to improve the diagnosis of extra-cardiac blood vessels using MRI (magnetic resonance imaging) as well as other imaging methods. The application with MRI is known in the art as MRA (magnetic resonance angiography), and includes applying a magnetic field to the region of interest, and mapping the effect of the magnetic field on various constituents of the region of interest. The technique is very useful, but the lengthy data acquisition time of the procedure causes blurring of the image is obtained. In order to improve the image, synchronizing the MR imaging with the heartbeat and other imaging methods or with the heartbeat as synchronized versus respiratory activity improves the clarity of the image.

The invention claimed is:

1. A method for analyzing a change in the functionality of the heart and the respiratory system of a patient, comprising:
    identifying the respiratory activity (22) and cardiac sounds (20), wherein said identifying comprises:
    1. collecting at least said cardiac sounds (20) by the means of at least one microphone;
    2. separating said cardiac sounds (20) apart from the sounds related to said respiratory activity (22), by the means of a signal conditioning module (28);
    temporally segmenting said respiratory and said cardiac sounds to express the segments of physiological rhythmicity, by the means of a feature extraction module (30);
    extracting stable features of the heart sounds with respect to their timing in the respiratory cycle, thus providing synchronized stable features for diminishing stochastic variability, by the means of a timing analysis module (32);
    averaging the features of segments of heart sounds with respect to the corresponding respiratory cycle; wherein the averaging results in averages in which the temporal variability of said segments is preserved;
    determining the extent of temporal variability in groups of synchronized stable sound features, and
    detecting change over time of at least one feature in a synchronized stable sound relative to a baseline, by the means of a temporal segmentation and feature parameter extraction module (34).

2. A method for analyzing a change in the functionality of the heart and the respiratory system of a patient as in claim 1, said method used for synchronizing a heartbeat synchronized system, said analyzing based on the information derived from the group of items consisting of: heart sounds amplitude, interval between them, amplitude and frequency content, and any combination thereof.

3. A method for analyzing a change in the functionality of the heart and the respiratory system of a patient, comprising:
    identifying the respiratory activity (22) and cardiac sounds (20), wherein said identifying comprises:
    1. collecting at least said cardiac sounds (20) by the means of at least one microphone;
    2. separating said cardiac sounds (20) apart from the sounds related to said respiratory activity (22), by the means of a signal conditioning module (28);
    temporally segmenting respiratory sounds and cardiac electrocardiographic signals to express the segments of physiological rhythmicity, by the means of a feature extraction module (30);
    extracting stable features of the heart sounds with respect to their timing in the electrocardiographic signals, thus providing synchronized stable features for diminishing stochastic variability, by the means of a timing analysis module (32);
    averaging the features of segments of heart sounds with respect to the corresponding electrocardiographic signals whilst preserving the temporal variability of said segments; wherein the averaging results in averages in which the temporal variability of said segments is preserved;
    determining the extent of temporal variability of groups of synchronized stable sound features, and
    detecting change over time of at least one feature in a synchronized stable sound relative to a baseline, by the means of a temporal segmentation and feature parameter extraction module (34).

* * * * *